(12) United States Patent
Petersen et al.

(10) Patent No.: US 8,871,955 B2
(45) Date of Patent: Oct. 28, 2014

(54) PROCESS FOR THE PURIFICATION OF PHARMACEUTICALLY ACCEPTABLE SALTS

(75) Inventors: Hans Petersen, Vanløse (DK); Martin Markvard Knudsen, Copenhagen (DK)

(73) Assignee: H. Lundbeck A/S, Valby (DK)

( * ) Notice: Subject to any disclaimer, the term of this patent is extended or adjusted under 35 U.S.C. 154(b) by 8 days.

(21) Appl. No.: 13/810,959

(22) PCT Filed: Jul. 12, 2011

(86) PCT No.: PCT/DK2011/050276
§ 371 (c)(1),
(2), (4) Date: Mar. 8, 2013

(87) PCT Pub. No.: WO2012/010174
PCT Pub. Date: Jan. 26, 2012

(65) Prior Publication Data
US 2013/0211107 A1      Aug. 15, 2013

Related U.S. Application Data

(60) Provisional application No. 61/366,954, filed on Jul. 23, 2010.

(30) Foreign Application Priority Data

Jul. 23, 2010   (DK) .................................. 2010 00678

(51) Int. Cl.
*C07D 307/87*        (2006.01)

(52) U.S. Cl.
CPC ................................. *C07D 307/87* (2013.01)
USPC .......................................................... 549/467

(58) Field of Classification Search
CPC .................................................... C07D 307/87
USPC .......................................................... 549/467
See application file for complete search history.

(56) References Cited

FOREIGN PATENT DOCUMENTS

| EP | 1988086 A1 | 11/2008 |
|---|---|---|
| WO | 03/007872 A2 | 1/2003 |
| WO | 03/072565 A1 | 9/2003 |
| WO | 2004/016602 A1 | 2/2004 |
| WO | 2005/049596 A1 | 6/2005 |
| WO | 2006/136169 A2 | 12/2006 |
| WO | 2010/004575 A2 | 1/2010 |

*Primary Examiner* — Taofiq A Solola
(74) *Attorney, Agent, or Firm* — Mary Catherine Di Nunzio

(57) ABSTRACT

The present invention is concerned with a process in connection with the purification of a pharmaceutically acceptable salt of escitalopram or citalopram.

13 Claims, 1 Drawing Sheet

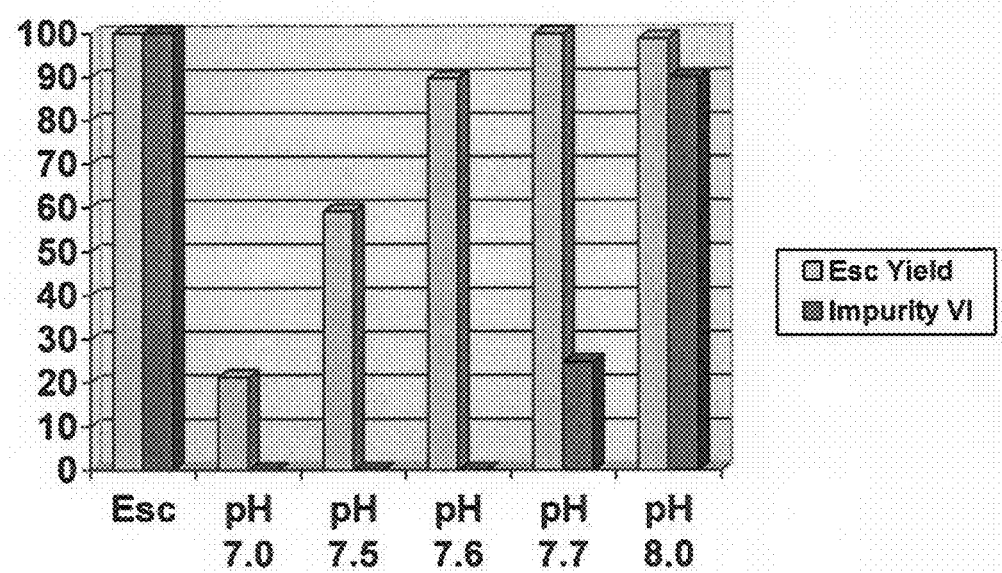

PROCESS FOR THE PURIFICATION OF PHARMACEUTICALLY ACCEPTABLE SALTS

CROSS-REFERENCE TO RELATED APPLICATIONS

The present application is a §371 U.S. National Stage Application of International Application No. PCT/DK2011/050276, filed Jul. 12, 2011, which claims the benefit of priority under 35 U.S.C. §119(e) of U.S. Provisional Application No. 61/366,954, filed Jul. 23, 2010 and which claims the benefit of priority under 35 U.S.C. §119(a)-(d) of Danish Patent Application No. PA201000678, filed Jul. 23, 2010. Each of these applications is hereby incorporated by reference in its entirety.

FIELD OF THE INVENTION

The present invention is concerned with a process of purifying a pharmaceutically acceptable salt of escitalopram or citalopram and, in particular, with the removal of diamine impurities formed in connection with the synthesis of said compounds.

BACKGROUND ART

Escitalopram, a selective serotonin re-uptake inhibitor, is a well known drug which has been on the market for the treatment of disorders relating to mood as well as anxiety. The structure of escitalopram is provided immediately below.

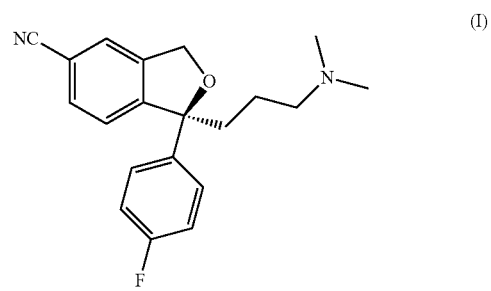 [SMILES: CN(C)CCC[C@@]1(c2ccc(F)cc2)OCc2cc(C#N)ccc21]

(I)

Citalopram is the racemate corresponding to escitalopram and was first disclosed in U.S. Pat. No. 4,136,193. Escitalopram was first disclosed in EP 0 347 066 and is currently marketed as an oxalate salt Since the publication of the above identified patents, a number of processes for the preparation and purification of escitalopram or pharmaceutically acceptable salts thereof have been devised.

One such preparation, as represented in scheme 1, involves starting with cyanophthalide. The Grignard condensation of 5-cyanophthalide with 4-fluorophenylmagnesium bromide gives 1-(4-fluorophenyl)-1-hydroxy-1, 3-dihydroisobenzofuran-5-carbonitrile bromo magnesium salt (II), which equilibrates to the benzophenone (III). A new Grignard condensation of (III) with 3-(dimethylamino)propylmagnesium chloride affords the bis(magnesium) salt, which is hydrolyzed with acetic acid to provide the diol (IV) as a racemic mixture (See U.S. Pat. No. 4,650,884 for details). The optical resolution of the racemic diol (IV) can be performed by HPLC via chiral labile ester derivatives or a resolution process using (+)-di-p-toluoyltartaric acid. The resulting (S)-diol (V) is cyclized by reaction with methanesulfonyl chloride to afford escitalopram. The free base can be converted to a pharmaceutically acceptable salt such as the oxalate.

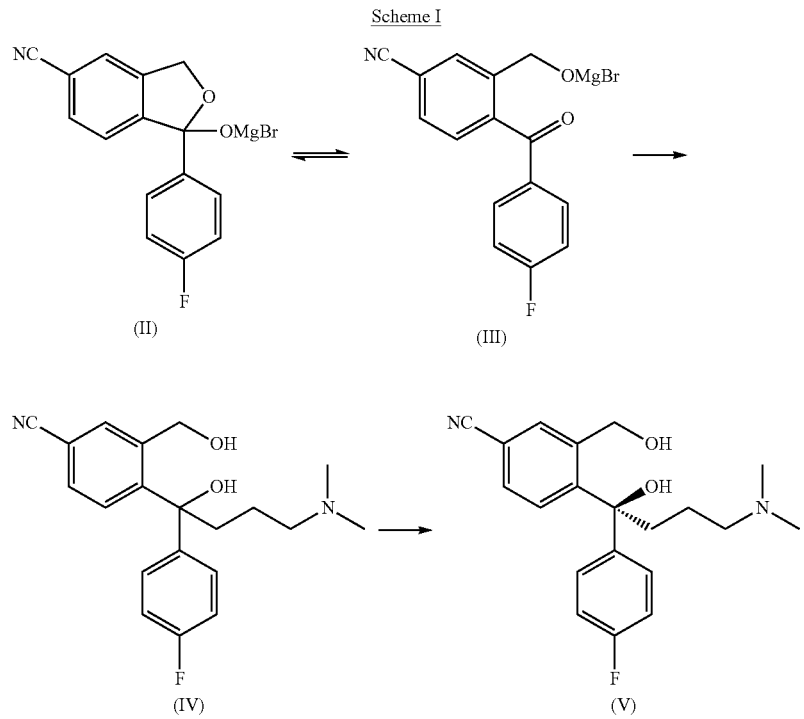

Scheme I

Unfortunately, and as is well-known in those skilled in the art impurities are inevitably formed during Grinard reactions and these impurities are difficult to separate from the desired end product. At times, extensive and time consuming purification procedures such as HPLC techniques are required to obtain purified escitalopram. Even by using a recrystallization procedure, the impurities remain in an undesired amount.

Where the production of escitalopram manufacture involves a procedure substantially similar to that described in scheme 1, the impurities as shown in the compounds of formulas VI-IX are:

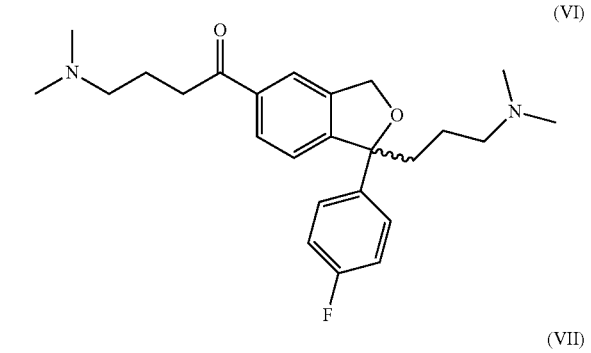

(VI)

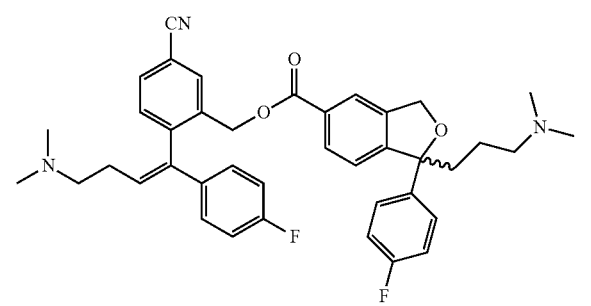

(VII)

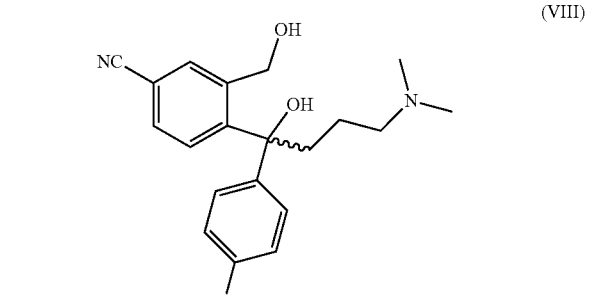

(VIII)

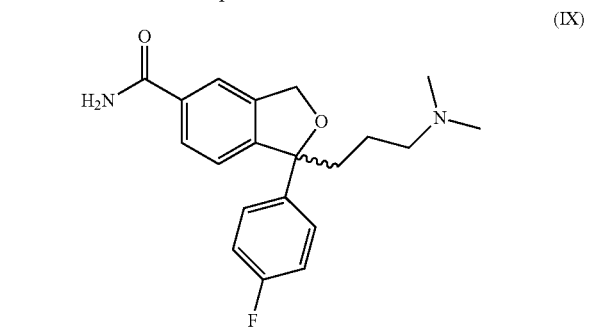

(IX)

Thus, there still remains the need to devise efficient and more economical purification procedures especially for use on an industrial scale where, for example, the use of HPLC may be prohibitively expensive and time consuming.

The inventors have now discovered an alternative process of purifying escitalopram by reducing the amount of the above mentioned impurities substantially without using potentially time consuming crystallization techniques or expensive HPLC techniques. Rather the inventors have found that by the careful selection of solvents and the careful manipulation of the pH, escitalopram may be isolated in very high purity while removing the impurity of formula VI as well as the impurity of formula VII in a desired amount.

SUMMARY OF THE INVENTION

Accordingly, an objective of the present invention is to provide a process for the purification of a crude mixture of a pharmaceutically acceptable salt of escitalopram comprising:
(a) dissolving said salt in water;
(b) adjusting the pH of the aqueous layer to 7.0-7.7 with a base;
(c) extracting said escitalopram with an organic solvent;
(d) isolating organic and aqueous layers;
(e) optionally repeating steps (b)-(d) one or more times on the isolated aqueous layer of step (d);
(f) combining organic extract layers and optionally washing organic layer with water, and
(g) isolating and optionally drying organic layer of step (f) and removing organic solvent.

A separate aspect of the invention concerns converting the purified escitalopram into a pharmaceutically acceptable salt.

Another aspect is of the invention is directed to the removal of diamine impurities from the crude mixture.

One aspect of the invention is directed to the removal of 4-dimethylamino-1-[1-(3-dimethylamino-propyl)-1-(4-fluoro-phenyl)-1,3-dihydro-isobenzofuran-5-yl]butan-1-one (VI) from the crude mixture.

Yet another aspect of the invention involves the removal of (Z)-1-{4-cyano-2-[({1-[3-(dimethylamino)propyl]-1-(4-fluorophenyl)-2-benzofuran-5-yl}carbonyloxy)methyl]phenyl}-4-(dimethylamino)-1-(4-fluorophenyl)but-1-en-2-yl (VII) from the crude mixture.

Another aspect of the invention relates to the removal of 4-dimethylamino-1-[1-(3-dimethylamino-propyl)-1-(4-fluorophenyl)-1,3-dihydro-isobenzofuran-5-yl]-butan-1-one (VI) and (Z)-1-{4-cyano-2-[({1-[3-(dimethylamino)propyl]-1-(4-fluorophenyl)-2-benzofuran-5-yl}-carbonyloxy)methyl]phenyl}-4-(dimethylamino)-1-(4-fluorophenyl)but-1-en-2-yl) (VII) from the crude mixture.

Embodiments of the present invention are provided in the detailed description.

BRIEF DESCRIPTION OF DRAWING

FIG. 1 provides a graphical representation of the removal of the impurity of formula VI from the crude mixture of escitalopram at different pH levels of the aqueous phase.

DETAILED DESCRIPTION OF THE INVENTION

As previously indicated, the present invention is based on the discovery of an industrially feasible process that can purify pharmaceutically acceptable salts of escitalopram or citalopram in an efficient and economical manner. The invention is explained in greater detail below but this description is not intended to be a detailed catalog of all the different ways in which the invention may be implemented, or all the features that may be added to the instant invention.

In step (a) of the process of the invention, the salt is dissolved in water at ambient temperature (22-25° C.) under atmospheric pressure.

In step (b), the base used to adjust the pH may be any conventional base. Suitable bases include $NH_4OH_{aq}$, NaOH and KOH and various organic bases. 16% $NH_4OH_{aq}$ is one base that can be used. According the invention, the pH should be adjusted between the range of 7.0 to 7.7.

However, one skilled in the art would recognize that the purification process can occur even through the pH of the aqueous layer is outside the range of 7.0 to 7.7 by adjusting the temperature of the solution. For example, if the pH of the aqueous layer is above 7.7, the temperature can be reduced accordingly to achieve the same result. Likewise, if the pH of the aqueous layer is below 7.0, the temperature can be increased accordingly to achieve the same result.

In steps (e) and (A) of the process, the escitalopram free base may be extracted from the aqueous solution by using an organic solvent. Suitable in this regard is toluene although other organic solvents such as xylene, hexane, heptane, pentanol etc. However, the organic solvent should not be miscible with water. For example, solvents such as methanol and ethanol are excluded from the scope of the invention since these solvents are miscible with water. Organic ester based solvents such as ethyl acetate and isopropyl acetate as well as organic ether based solvents such as diethylether and t-butylmethylether can also be employed. The organic and aqueous layers formed should be separated by a simple layer separation procedure.

In order to extract escitalopram, the steps (b)-(d) can be repeated one or more times to obtain an optimal yield.

In step (f), the organic extracts are combined and washed with water.

And in step (g), the organic and aqueous layers formed should be separated by a simple layer separation procedure and optionally dried with for example sodium sulfate. Said organic solvent can be removed under reduced pressure using standard techniques or by other well known methods.

The purification technique of the present invention is suitable for preparing escitalopram where the crude mixture has been prepared via the double Grignard condensation of 5-cyanophthalide or a substantially similar synthesis thereof. However, the process is equally suitable for the purification of the crude mixture of escitalopram or citalopram made by any other process.

Embodiments of the present invention are provided immediately below.

In one embodiment, the purification involves the removal of 4-dimethylamino-1-[1-(3-dimethylamino-propyl)-1-(4-fluoro-phenyl)-1,3-dihydro-isobenzofuran-5-yl]-butan-1-one (VI) from the crude mixture.

In another embodiment, the purification involves the removal of (Z)-1-{4-cyano-2-[({1-[3-(dimethylamino)propyl]-1-(4-fluorophenyl)-2-benzofuran-5-yl}carbonyloxy)methyl]phenyl}-4-(dimethylamino)-1-(4-fluorophenyl)but-1-en-2-yl (VII) from the crude mixture.

In individual embodiments, the purification involves the removal of the impurity of formula VI, formula VII, formula VIII and/or formula IX.

In another embodiment, the pharmaceutically acceptable salt is an oxalate.

In a separate embodiment, the base is $NH_4OH_{aq}$.

In another embodiment, the concentration of $NH_4OH_{aq}$ is 16%

In yet another embodiment, the organic solvent is hydrocarbon based.

In another embodiment, the organic solvent is toluene.

In a separate embodiment, the total of number extractions is not more than 3.

In a separate embodiment, the total of number extractions is not more than 5.

In a separate embodiment, the total of number extractions is in the range of 6-15.

In a separate embodiment, the total of number extractions is in the range of 8-12.

In a separate embodiment, the pH is adjusted to a range from 7.1 to 7.7.

In a separate embodiment, the pH is adjusted to a range from 7.2 to 7.6.

In one embodiment, the pH is adjusted to a range from 7.3 to 7.6.

In a separate embodiment, the pH is adjusted to a range from 7.4 to 7.6.

In a separate embodiment, the pH is adjusted to a range from 7.5 to 7.6.

In yet another embodiment, the pH is adjusted to about 7.0, 7.1, 7.2, 7.3, 7.4 or 7.5. In another embodiment, the pH is adjusted to about 7.6 or 7.7.

DEFINITIONS

As used herein, a crude mixture of a pharmaceutically acceptable salt of escitalopram contains one or more of the impurities of VI, VII, VIII or IX in an undesired amount.

An undesired amount of impurity, as used herein, corresponds to >0.05% weight of the final product. A narrower limit of the undesired amount of impurity corresponds to >0.01%.

As used herein, the term a suitable base includes $NH_4OH_{aq}$, NaOH and KOH and various inorganic and organic bases. One skilled in the art can identify which bases are suitable for the instant invention.

The impurity of formula VI is 4-dimethylamino-1-[1-(3-dimethylamino-propyl)-1-(4-fluorophenyl)-1,3-dihydro-isobenzofuran-5-yl]-butan-1-one.

The impurity of formula VII is (Z)-1-{4-cyano-2-[({1-[3-(dimethylamino)propyl]-1-(4-fluorophenyl)-2-benzofuran-5-yl}carbonyloxy)methyl]phenyl}-4-(dimethylamino)-1-(4-fluorophenyl)-but-1-en-2-yl.

Escitalopram and citalopram form pharmaceutically acceptable acid addition salts with a wide variety of organic and inorganic acids and include the physiologically acceptable salts which are often used in pharmaceutical chemistry. Such salts are also part of this invention. Such salts include the pharmaceutically acceptable salts listed in Journal of Pharmaceutical Science, 66, 2-19 (1977) which are known to the skilled artisan.

Typical inorganic acids used to form such salts include hydrochloric, hydrobromic, hydroiodic, nitric, sulfuric, phosphoric, hypophosphoric, metaphosphoric, pyrophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used.

Such pharmaceutically acceptable salts thus include chloride, bromide, iodide, nitrate, acetate, phenylacetate, trifluoroacetate, acrylate, ascorbate, benzoate, chloroberizoate, dinitrobenzoate, hydroxybenzoate, methoxybenzoate, methylbenzoate, o-acetoxybenzoate, isobutyrate, phenylbutyrate, a-hydroxybutyrate, butyne-1,4-dicarboxylate, hexyne-1,4-dicarboxylate, caprate, caprylate, cinnamate, citrate, formate, fumarate, glycollate, heptarioate, hippurate, lactate, malate, maleate, hydroxymaleate, malonate, mandelate, mesylate, nicotinate, isonicotinate, oxalate, palmate, phthalate, teraphthalate, propiolate, propionate, phenylpropionate, salicylate, sebacate, succinate, suberate, benzenesulfonate, p-bromobenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, p-toluenesulfonate, xylenesulfonate, tartrate, and the like.

Escitalopram or pharmaceutically acceptable salts thereof which are made by the process of the invention may be formulated into pharmaceutical compositions as is well known in the art. Such compositions may take the form of tablets which may be prepared by mixing the active ingredient with ordinary adjuvants and/or diluents and subsequently compressing the mixture in a conventional tableting machine. Examples of adjuvants or diluents comprise: corn starch, potato starch, talcum, magnesium stearate, gelatin, lactose, gums and is the like. Any other adjuvant or additive colourings, aroma, preservatives, taste masking agents etc. may be used provided that they are compatible with the active ingredient.

Alternatively, the free base of escitalopram can be used instead of a pharmaceutically acceptable salt in connection with its medicinal use.

The active ingredient may also be formulated as a solution for injection which may be prepared by solving the active ingredient and possible additives in a part of the solvent for injection, preferably sterile water, adjusting the solution to the desired volume, sterilisation of the solution and filling in suitable ampoules or vials. Again, any suitable additive conventionally used in the art may be added such as tonicity agents, preservatives, antioxidants, etc.

The amount of escitalopram administered to a patient is dependent on the nature of the patient and will be readily determined by the skilled physician. Tablets may however comprise, for example, 10 mg or 20 mg doses.

Experimental Section

HPLC Conditions:

The HPLC analysis was made under the following chromatographic conditions; column: XBridge $C_{18}$ (150×2.1 mm ID 3.5 μm). Mobile phase A: 200 mM ammonium formate buffer pH 3.0/water/Acetonitrile (5/85/10). Mobile phase B: 200 mM ammonium formate buffer pH 3.0/water/Acetonitrile (5/15/80). Flow: 0.25 ml/mm. Temperature: 45° C. Injection volume: 4 μl. Detection: 237 nm, bandwidth 4 nm.

Agilent MSD-1100 was used to detect the impurities of formulas VI-IX from escitalopram. The lower level of detection (LLOD) is about 5 ppm.

| Gradient profile: | Time (min) | Phase B (%) |
|---|---|---|
| | 0.0 | 10.0 |
| | 2.0 | 10.0 |
| | 17.0 | 42.9 |
| | 27.0 | 85.7 |
| | 32.0 | 85.7 |
| | 32.1 | 10.0 |
| Run time: | 50 min | |

The invention is further described with reference to the following non-limiting examples.

Example 1a

Crude escitalopram oxalate can be prepared according to the procedure set forth in EP 0 347 066. The amount of the impurity of formula VI used in examples 1a-1e present was determined to be about 529 ppm.

Crude escitalopram oxalate (10 g) as stirred in water (100 ml) at room temperature and the pH of the solution was adjusted to 7.0 by the addition of 16% $NH_4OH_{aq}$. The aqueous solution was extracted with toluene (100 ml) and the aqueous and organic layers were separated. The pH of the aqueous layer was readjusted to 7.0 by the further addition of 16% $NH_4OH_{aq}$ and extracted with toluene (100 ml). This extraction procedure was repeated for a total of 3 extractions. The three toluene extracts were combined, ashed with water (100 ml), dried with $Na_2SO_4$ and concentrated in-vacuo to afford the free base as an oil (yield: 1.66 g 21.2%). Analysis of the obtained free base indicated that the impurity of formula VI was below the LLOD (Lowest Level of Detection).

Example 1b

Using the same batch of crude escitalopram oxalate (10 g), Example 1a was repeated whereby the pH was instead adjusted to 7 to afford the end product yield: 4.62 g 59.1%). Using this pH, the impurity of formula VI was determined to be below the LLOD.

Example 1c

Using the same batch of crude escitalopram oxalate (10 g). Example 1a was repeated whereby the pH was instead adjusted to pH 8.0 to afford the end product (yield: 7.72 g/98.7%). Using this pH, the impurity of formula VI was determined to be ~467 ppm.

Example 2a

Crude escitalopram oxalate can be prepared according to the procedure set forth in EP 0 347 066. The amount of the impurity of formula VI present used in examples 2a-2c was determined to be about 515 ppm.

This purification process used for examples 2a-2c was similar to that of example 1a-1c and the crude mixture of escitalopram used was 10 g. The pH was adjusted to 7.5. However, the total number of extractions was repeated for a total of 5 extractions. Accordingly, the five toluene extracts were combined, washed with water (100 ml), dried and concentrated in-vacuo to afford the end product (yield: 5.55 g 70.9%). Analysis of the obtained free base indicated that the impurity, of formula VI was below the LLOD.

Example 2b

Using the same batch of crude escitalopram oxalate (10 g), Example 2a was repeated whereby the pH was instead adjusted to 7.6 to afford the end product (yield: 7.01 g/89.6%). Using this pH, the impurity of formula VI was determined to be below the LLOD.

Example 2c

Using the same batch of crude escitalopram oxalate (10 g). Example 2a was repeated whereby, the pH was instead adjusted to 7.7 to afford the end product (yield: 7.82 g 99.9%). Using this pH, the impurity of formula VI was determined to be ~129 ppm.

FIG. 1 provides a graphical representation of level of purification occurring at different pH values of the aqueous phase. The amount of the impurity of formula VI has been normalized to a value of 100, which corresponds to about 520 ppm.

The data in examples 1 and 2 indicate that the process run at pH 7 removes the impurity of formula VI but affords a lower yield of escitalopram. On the other end, the process run at pH 8.0 appears not to remove the impurity of formula VI. However, processes run at a range from about pH 7.5 to about 7.6 provides removal of the impurity in a desired amount while maintaining high yields.

Example 3a

Crude escitalopram oxalate can be prepared according to the procedure set forth in EP 0 347 066. The amount of the crude mixture of escitalopram used was 10 g and the impurity of formula VII present was determined to be about 890 ppm.

The purification process used was similar to that of example 2a-2c with the pH adjusted to 7.4. Accordingly, the five toluene extracts were combined, washed with water (100 ml), dried and concentrated in-vacuo to afford the free base (yield: 3.56 g/46.7%). Analysis of the obtained end product indicated that the impurity of formula VII was determined to be 72 ppm, which is a reduction in the amount of impurity by a factor of 12.4.

Example 3b

Crude escitalopram oxalate can be prepared according to the procedure set forth in EP 0 347 066. The amount of crude mixture of escitalopram used was 10 g and the impurity of formula VII present was determined to be about 930 ppm.

The purification process used was similar to that of example 2a-2c with the pH adjusted to 7.6. Accordingly, the five toluene extracts were combined, washed with water (100 ml), dried and concentrated in-vacuo to afford the free base (yield: 88.9%). Analysis of the obtained end product indicated that the amount of the impurity of Formula VII was determined to be 514 ppm.

Example 4

This example describes how the removal of the impurity of formula (VI) from a full scale (278.6 kg) batch escitalopram oxalate is performed.

Escitalopram oxalate (278.6 kg) containing 1000 ppm of the impurity of formula (VI) is dissolved in water (1400 L) and the mixture is heated to 45° C. The pH is adjusted to 7.2 by addition of 25% aqueous ammonia. To the solution is added 1400 L toluene and the mixture is heated to 45° C. with stirring for 10-20 minutes and then left to settle for at least 10 minutes and the toluene and water phases are separated into two different reactors. By HPLC the amount of the impurity of formula (VI) relative to escitalopram is determined in the organic phase (<LOQ (Level Of Quantification)).

The aqueous phase is once again heated to 45° C., pH is adjusted to 7.2 with 25% aqueous ammonia and then toluene is added, followed by mixing and phase separation. This procedure is repeated ten times in total.

In the final combined toluene phase the amount of the impurity of formula (VI) is 230 ppm. The combined toluene phases contained 190.8 kg escitalopram (free base) corresponding to a molar yield of 87.3%.

What is claimed:

1. A process for the purification of a crude mixture of a pharmaceutically acceptable salt of escitalopram comprising:
   a. dissolving said salt in water;
   b. adjusting the pH of the aqueous layer to 7.0-7.7 with a base;
   c. extracting said escitalopram with an organic solvent;
   d. isolating organic and aqueous layers;
   e. repeating steps (b)-(d) on the isolated aqueous layer of step (d);
   f. combining organic extract layers and optionally washing organic layer with water; and
   g. isolating and optionally drying the organic layer of step (f) and removing the organic solvent,
   wherein the organic solvent is not miscible with water and wherein the process involves the removal of diamine impurities from the crude mixture.

2. The process of claim 1, wherein the pharmaceutically acceptable salt is an oxalate.

3. The process of claim 1, wherein the base is NH4OHaq.

4. The process of claim 1, wherein the organic solvent is toluene.

5. The process of claim 1, wherein the total number of extractions is not more than 3.

6. The process of claim 1, wherein the total number of extractions is not more than 5.

7. The process of claim 1, wherein the total number of extractions is in the range of 6-15.

8. The process of claim 1, wherein the total number of extractions is in the range of 8-12.

9. The process of claim 1, wherein the pH is adjusted to a range from 7.1 to 7.7.

10. The process of claim 7, wherein the pH is adjusted to a range from 7.2 to 7.7.

11. The process of claim 8, wherein the pH is adjusted to a range from 7.3 to 7.6.

12. The process of claim 9, wherein the pH is adjusted to a range from 7.4 to 7.6.

13. The process of claim 10, wherein the pH is adjusted to a range from 7.5 to 7.6.

* * * * *